United States Patent [19]
Verduijn et al.

[11] Patent Number: 5,849,967
[45] Date of Patent: Dec. 15, 1998

[54] HYDROCARBON CONVERSION PROCESS USING BINDERLESS ZEOLITE L CATALYST

[75] Inventors: Johannes Petrus Verduijn, Spijkenisse; Pieter Ernst Gellings, Oostvoorne, both of Netherlands

[73] Assignee: Exxon Chemical Patents Inc. (ECPI), Wilmington, Del.

[21] Appl. No.: 473,835

[22] Filed: Jun. 7, 1995

Related U.S. Application Data

[62] Division of Ser. No. 320,972, Oct. 12, 1994, Pat. No. 5,486,348, which is a continuation of Ser. No. 121,972, Sep. 15, 1993, abandoned, which is a continuation of Ser. No. 492,249, Mar. 9, 1990, abandoned, which is a continuation of Ser. No. 160,366, Feb. 25, 1988, abandoned.

[30] Foreign Application Priority Data

Feb. 25, 1987 [GB] United Kingdom .................. 8704365

[51] Int. Cl.$^6$ ...................................................... C07C 2/00
[52] U.S. Cl. ......................... 585/407; 585/415; 585/427; 585/428; 585/481
[58] Field of Search .................................. 585/428, 427, 585/407, 481, 415

[56] References Cited

U.S. PATENT DOCUMENTS

| | | | |
|---|---|---|---|
| 4,544,539 | 10/1985 | Wortel | 423/328 |
| 5,486,348 | 1/1996 | Verduijn et al. | 423/700 |

FOREIGN PATENT DOCUMENTS

| | | |
|---|---|---|
| 0 142 349 | 5/1985 | European Pat. Off. |
| 1092681 | 11/1967 | United Kingdom |

*Primary Examiner*—Asok Pal
*Attorney, Agent, or Firm*—Edward F. Sherer

[57] ABSTRACT

Binderless zeolite L particles are prepared by a method in which particles are formed from silica and from 0 to 95 wt % preformed zeolite L crystallites, and the particles are thereafter reacted with an alkaline solution comprising a source of alumina to convert the silica binder to zeolite L. These particles may comprise cylindrical zeolite L crystallites with a mean diameter of at least 0.05 micron in a zeolite L matrix and may be used as catalyst. Also acyclic hydrocarbons are dehydrocyclized and/or isomerized by contacting them at a temperature of from 370° C. to 600° C. with this catalyst incorporating at least one Group VIII metal having dehydrogenating activity to convert at least part of the acyclic hydrocarbons into aromatic hydrocarbons.

10 Claims, 1 Drawing Sheet

HYDROCARBON CONVERSION PROCESS USING BINDERLESS ZEOLITE L CATALYST

This application is a divisional of pending application Ser. No. 08/320,972, filed Oct. 12, 1994, now U.S. Pat. 5,486,348 which is a continuation of Ser. No. 08/121,972, filed Sep. 15, 1993, now abandoned, which is a continuation of Ser. No. 07/492,249, filed Mar. 9, 1990, now abandoned, which is a continuation of Ser. No. 07/160,366, filed Feb. 25, 1988, now abandoned.

BACKGROUND OF THE INVENTION

1. Field of the Invention

This invention relates to the preparation of substantially binderless particles of zeolite L, particularly in the form of aggregates for use in catalysis, particularly for aromatization.

2. Description of Related Art

Zeolite L has been known for some time as an adsorbant, and in U.S. Pat. No. 3,216,789 is described as an aluminosilicate of the formula:

$$0.9\text{--}1.3\ M_{2/n}O: Al_2O_3:5.2\text{--}6.9\ SiO_2yH_2O$$

(where M is an exchangeable cation of valence n and y is from 0 to 9) having a characteristic X-ray diffraction pattern. The preparation of zeolite L described in U.S. Pat. No. 3,216,789, EP-A-167755, EP-A-142355, EP-A-142347, EP-A-142349, EP-A-109199, PL-A-72149, U.S. Pat. No. 3,867,512, and SU-548567.

EP-A-96479 describes and claims zeolite L having a characteristic morphology and size, which is particularly valuable for use as a catalyst base in hydrocarbon conversions such as aromatization, and comprising crystallites in the form of cylinders with a mean diameter of at least 0.1 micron, preferably at least 0.5 micron.

EP-A-96479 describes a synthesis of zeolite L which is conducted so that the amount of the contaminant zeolite W, which is known to grow in such a system as a competitive phase, is minimised. A preferred synthesis gel described in EP 96479 has the following mole ratios:

$$2.6K_2O:Al_2O_3:10SiO_2:160H_2O$$

and it is discussed how this gel may be varied by changing the molar amount of one component within the following ranges:

K$_2$O: 2.4–3.0 moles
Al$_2$O$_3$: 0.6–1.3 moles
SiO$_2$: 8–12 moles
H$_2$O: 120–240 moles EP-A-142353, EP-A-142354 and EP-A-185519 describe developments of this process for forming cylindrical zeolite L.

Zeolite L may be used as a catalyst base in aromatization reactions. U.S. Pat. No. 4,104,320 discloses dehydrocyclization of aliphatic compounds in the presence of hydrogen using a catalyst comprising zeolite L and a group VIII metal. The particular zeolite disclosed in EP 96479 is remarkably effective in such aromatization reaction being capable of forming catalysts which have extended lifetime. Such dehydrocyclization and/or aromatization reactions and catalysts for use in such reactions are also described in EP-A-107389, EP-A-184451, EP-A-142351, EP-A-145289, EP-A-184450, U.S. Pat. No. 4,614,834, GB-A-2116450, GB-A-2114150, U.S. Pat. Nos. 4,458,025, 4,456,527, GB-A-2142648, GB-A-2106483, U.S. Pat. No. 4,443,326, GB-A-2121427, GB-A-2153840, GB-A-2153384, U.S. Pat. Nos. 4,517,306, 4,539,304, 4,539,305, 4,547,472, GB-A-2166972, U.S. Pat. Nos. 4,579,831, 4,608,356 and EP-A-201856.

The product recovered from the usual methods used to prepare zeolite L is a fine sized crystalline material. Several of the uses as catalysts or molecular sieves require a product in a size range substantially larger than the size of the product recovered from the preparation processes of the prior art. To meet this demand, various binders are used in forming steps to prepare aggregates containing zeolite L as the principal ingredient such as pellets, extrudates, or tablets. These aggregates lose some of their activity per unit weight since the binder has a different and low activity and acts as a diluent of the molecular sieve activity and the conventionally-bound aggregates frequently do not have sufficient crushing strength, particularly when they contain the cylindrical zeolite L crystallites as described in EP-A-96479. In addition particles made using alumina as binder are susceptible to blocking of the zeolite pores, as a result of alumina migration. It is therefore highly desirable to develop a method of preparing binderless aggregates having a particle size suitable for catalyst or sieve systems and possessing good attrition resistance.

The prior art has developed processes of producing binderless sieve aggregates from silica and alumina starting materials such as silica-alumina catalysts and clay. Unfortunately the products produced by these processes, especially where clay is used as a starting material, generally have very poor attrition resistance and thus rapidly break during use into unsuitable powers which must be replaced.

U.S. Pat. No. 3,650,687 describes processes for the preparation of binderless zeolite particles including zeolite L, in which an alumina silicate clay is slurried with an alkali silicate, spraydried to form particles of the desired finished size and then treated with alkali and aged to convert the particles to zeolite. In an alternative, a hydrated clay is slurried and spraydried to form particles, then calcined and reacted with the other components necessary to form a zeolite. Thus zeolite is only formed after the final particles have been formed. Predictable formation of zeolite having optimum catalytic properties may be difficult under such circumstances.

Also spray drying can be used only to give small particles, typically of 100 to 400 microns, which are only suitable for fluidized beds whereas reactors usually need particle sizes of at least 0.8 mm, preferably at least 1.5 mm and typically 3 mm.

GB-A-1316311 describes binderless zeolite particles which may be of zeolite L, and which are formed by pelleting, crush and repelleting repeatedly to give products of the desired strength. This is a time-consuming procedure which is costly and can damage the zeolite crystals.

GB-A-2109359 describes preparation of zeolite 3A and 4A binderless particles in various processes in which kaolin clay and sodium hydroxide (in some cases with zeolite) are formed into beads and then reacted with further sodium hydroxide to from zeolite 4A (sodium form) which is exchanged to form zeolite 3A (potassium form). It is clearly stated that direct formation of a potassium zeolite is not possible in this process.

GB-A-2160517 describes the formation of so called preformed zeolite particles, which may be zeolite L particles prepared from a starting material, which may be a synthetic zeolite but must have a silica/alumina ratio lower than the product. The starting material is reacted with a silica material and an alkali to form the product. To form zeolite L either zeolite 3A, kaolin or a silica-alumina starting material is used. The products are necessarily more silica rich than the starting zeolite. This process has practical handling problems in treating particles with a silica containing material.

GB-A-979398 describes the formation of so-called self-bonded pellets of mordenite, in which a powdered aqueous mixture of sodium oxide, alumina and silica are pelleted, heated and then heated with sodium silicate and/or caustic soda to form mordenite. Mordenite has a different chemical composition and crystalline structure to zeolite L.

The prior art systems are either unsuitable for providing binderless particles of zeolite L having high catalytic or adsorbant activity, or result in particles of inadequate strength to be suitable for handling in practical applications or are impractical for large scale operation.

SUMMARY OF THE INVENTION

The invention concerns a method of preparing binderless zeolite L particles without undesirable loss of catalytic performance and/or capacity and with excellent physical strength, for example against attrition.

Thus, in one aspect the invention provides method of preparing binderless zeolite L particles, in which particles are formed from silica and from 0 to 95 wt % preformed zeolite L crystallites, and the particles are thereafter reacted with an alkaline solution comprising a source of alumina to convert the silica binder to zeolite L.

DETAILED DESCRIPTION OF THE INVENTION

Figure 1C:
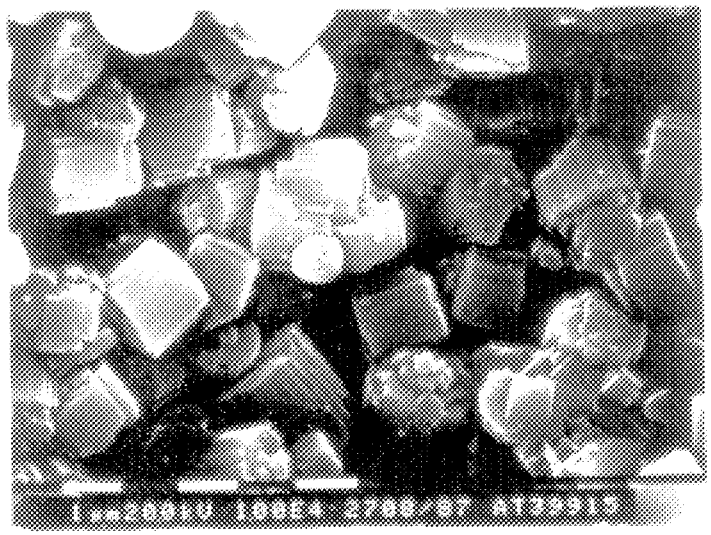
FIG. 1c shows binderless zeolite L particles of the invention as prepared in accordance with Ex. 1C.

When used herein in relation to the invention the term "binderless zeolite L particles" refers to a plurality of individual zeolite L crystallites held together without the use of a significant amount of non-zeolitic binder. Preferably the particles contain less than 10 wt % (based on the weight of the total particles) of non-zeolitic binder, such as the silica used in formation of the particles. More preferably, the particles contain less than 5 wt % of non-zeolitic binders, and it is most preferable for the particles to be substantially free of non-zeolitic binder.

The zeolite L crystallites used as starting material may be prepared by any of the known procedures, such as those described in the patents identified hereinbefore as relating to zeolite L preparation. However, it is highly preferred that the zeolite L should be in a form having beneficial effects on the catalytic performance of the zeolite. Thus, it is a surprising feature of the invention that the starting material may be a zeolite comprising crystallites in the form of cylinders with a mean diameter of at least 0.05 micron, preferably at least 0.1 micron, typically at least 0.5 micron, such as described in EP-A-96479, and most preferably the crystallites have the basal planes shaped such that the ratio of axial length of curved cylindrical surface (1) to the overall axial length of the crystallite (h) is greater than 0.9, optimally substantially unity. It is believed that this preferred aspect of the invention provides binderless zeolite L particles comprising such cylindrical crystallites in a zeolite L matrix which are themselves novel, and surprising given the difficulty of aggregating cylindrical crystallites, and so in another aspect this invention provides these novel particles per se. However, the invention is of broader application and may be used with zeolite L crystallites of other morphologies.

The zeolite L used as starting material, and in the final particle, is preferably an aluminosilicate and will be described hereinafter in terms of being an aluminosilicate, though other elemental substitutions are possible, for example aluminium may be substituted by gallium, boron, iron and similar trivalent elements, and silicon may be substituted by elements such as germanium or phosphorus. The aluminosilicates preferably have a composition (expressed in terms of molar ratios of the constituent oxides in anhydrous form) of:

$$(0.9-1.3) \, M_{2/n}O : Al_2O_3 : xSiO_2 \qquad (I)$$

wherein M is a cation of valence n, x is from 4 to 7.5, preferably from 5 to 7.5. The zeolite L preferable has high crystallinity as shown by a well defined X-ray diffraction pattern with sharp peaks.

The exchangeable cation M is very preferably potassium, but is is possible for a part of M to be replaced by other cations such as alkali and alkaline earth metals for example sodium, rubidium, caesium. The zeolite L may also contain, preferably at non-exchangeable sites, copper, calcium, barium, leads manganese, chromium, cobalt, nickel or zinc.

The zeolite L used in the invention may be hydrated, typically with from 0 to 9 moles of water per mole of $Al_2O_3$, and the binderless zeolite L particles will usually be hydrated. When used as a catalyst base, as described hereinafter, the zeolite of the invention is preferably first calcined to remove water.

In a modification of the method of the invention the particles formed from silica and preformed zeolite L crystallites are ground to finer particles of silica-bound zeolite L. These finer particles result in finer particles of binderfree zeolite L.

The preformed zeolite L crystallites are present in an amount of from 0 to 95 wt % of the initial particles—that is, the particles contain from 5 to 100 wt % of non-zeolitic material before reaction to convert the non-zeolitic material to zeolite. It is possible to form particles of the invention from initial particles comprising no zeolite L. However, it is preferable for there to be from 10 wt % to 50 wt % of preformed zeolite L crystallites in the initial particles. Small amounts of lubricants may be present to help in the formation of the particles, e.g. aluminium stearate or graphite, but preferably such additional materials are present in amounts of less than 5 wt %, more preferably less than 2 wt %, of the particles.

The silica, and very preferably preformed zeolite L crystallites, and optionally lubricant, are formed into particles of the desired shape and size. These may be tablets, pellets, extrudates or other agglomerated forms, and the machinery and techniques involved in forming these particles are well known and within the competence of one skilled in the art. Typically, the particles would have a size of at least 200 micron and for catalytic applications may be from 0.1 to 10 mm maximum size in any one direction, usually from 1 to 5 mm.

Following formation of the particles, they are reacted with an alkaline solution comprising an alumina source to convert the silica to zeolite L. The composition of the alkaline solution will be selected to form with the silica a reaction mixture capable of forming zeolite L. The principal components of the alkaline solution will generally be:

| | |
|---|---|
| aluminium | |
| potassium | (optionally with up to 30 mole % replaced by alkali or alkaline earth metal) |
| water | | and optionally additional metals such as copper, magnesium, calcium, barium, manganese, chromium, cobalt, nickel, lead or zinc.

The combined composition of the alkaline solution and the silica in the initial particles is preferably within the following molar ratios (expressed as oxides):

| | |
|---|---|
| $(M_2O + M^1_{2/n}O).SiO_2$ | 0.18–0.36, preferably 0.25–0.35 |
| $H_2O/(M_2O + M^1_{2/n}O)$ | 25–90 |
| $SiO_2/Al_2O_3$ | 4–15, preferably 5–15, more preferably 5–8 |
| $M_2O/(M_2O + M^1_{2/n}O)$ | 0.9–1 |

(Wherein M is potassium, optionally replaced by up to 30 mole % of another alkali metal, $M^1$ is copper, magnesium, calcium, barium, lead, manganese, chromium, cobalt, nickel or zinc cation and n is the valence of $M^1$). The particles are preferably heated in the alkaline solution to a temperature of at least 75° C. and preferably from 100° C. to 250° C., more preferably from 120° C. to 225° C., to form the binderless zeolite L particles of the invention.

Preferably the composition of the combined alkaline solution and the silica is 2.5–3.2 $K_2O$/1.5–2.5 $Al_2O_3$/10 $SiO_2$/120–180 $H_2O$. The preferred composition is alumina rich relative to preformed zeolite L crystallites—that is, produces a zeolite L product having a $SiO_2/Al_2O_3$ ratio equal to or lower than that of the preformed zeolite L crystallites—and surprisingly this results in a more complete conversion of the silica binder, and a stronger final product is obtained in terms of crushing strength and attrition.

The source of aluminium may be an alumina introduced into the reaction medium as, for example, $Al_2O_3 \cdot 3H_2O$, previously dissolved in alkali, thus as potassium aluminate. However, it is also possible to introduce aluminium in the form of the metal, which is dissolved in alkali.

The potassium in the reaction mixtures is preferably introduced as potassium hydroxide but may also be introduced as other salts such as the nitrate, chloride or sulphate. The reaction mixture may contain small quantities of other metal cations and salt forming anions as already described, but it has been found that there is an increasing tendency for other alumino-silicates to be found as the content of the other ions is increased, resulting in less pure forms of the alumino-silicate of the invention. For example, excess sodium and rhubidium ions favour zeolite W and/or erionite formation.

The product of the processes described above is predominantly a potassium form of the zeolite L. By ion exchange of the product in the manner conventional to zeolite chemistry other cations such as Na or H can be introduced.

Crystallization time is related to the crystallization temperature. The crystallization is preferably carried out at from 100° to 200° C. and at this temperature the crystallization time may be from 15 to 96 hours, for example from 48 to 72 hours, with shorter times being possible with higher temperatures and/or higher alkalinity ($K_2O/SiO_2$). Lower temperatures may require much longer times and may also require adjustment of alkalinity to achieve good yield of the desired product, whereas times of less than 24 hours are possible when higher temperatures are used. A time of 8 to 15 hours is typical for a temperature of greater than 200° C.

The crystallization is generally carried out in a sealed autoclave and thus at autogenous pressure. It is generally inconvenient, although possible to employ higher pressures. Lower pressure (and lower temperature) will require longer crystallization times.

Following the preparation as described above the zeolite may be separated, washed and dried in the normal manner.

When the binderless particles so prepared are in the form of finer particles (when first formed particles of silica and zeolite L have been ground before being converted to binderfree particles), these finer binderfree particles may in turn be formed into larger shaped particles by the use of conventional binder techniques or by a binderless process such as described herein.

We have found that the binderless zeolite L particles prepared by the invention are excellent catalyst bases and may be used in conjunction with one or more catalytically-active metals in a wide variety of catalytic reactions. The particular morphology of the crystals appears to result in a particular stable base for catalytically active metals with a surprising resistance to metal catalyst deactivation. Also the particles have increased toluene adsorption capacity as compared to conventionally bound zeolite L, together with increased particle strength. In addition, they have displayed low acidity which makes them especially suited to catalytic applications where a low acid site strength is advantageous such as aromatization.

The catalytically-active metal(s) may be, for example, a Group VIII metal such as platinum, tin, or germanium as described in U.S. Pat. No. 4,104,320, or a combination of platinum and rhenium as described in GB 2 004 764 or BE 888365. In the latter case the catalyst may for appropriate circumstances also incorporate halogen as described in U.S. Pat. No. 4,165,276, silver as described in U.S. Pat. Nos. 4,295,959 and 4,206,040, cadmium as described in U.S. Pat. Nos. 4,295,960 and 4,231,897 or sulphur as described in GB 1 600 927.

We have found a particularly advantageous catalyst composition to incorporate from 0.1 to 6.0 weight %, preferably from 0.1 to 1.5 weight % platinum or palladium, since this gives excellent results in aromatization. From 0.4 to 1.2 wt % platinum is particularly preferred, especially in conjunction with the potassium form of the aluminosilicate. The invention extends to catalysts comprising the zeolitic material and a catalytically-active metal.

The products of the invention may be used in a process for the conversion of a hydrocarbon feed in which the feed is contacted with a catalyst as described above under appropriate conditions to bring about the desired conversion. They may for example be useful in reactions involving aromatization and/or dehydrogenation reaction. They are particularly useful in a process for the dehydrocyclization and/or isomerization of acyclic hydrocarbons in which the hydrocarbons are contacted at a temperature of from 370° C. to 600° C., preferably from 430° C. to 550° C. with a catalyst comprising binderless zeolite L particle of the invention preferably having at least 90% of the exchangeable cations as alkali metal ions and incorporating at least one Group VIII metal having dehydrogenating activity, so as to convert at least part of the acyclic hydrocarbons into aromatic hydrocarbons.

The aliphatic hydrocarbons may be straight or branched chain acyclic hydrocarbons, and particularly paraffins such as hexane, although mixtures of hydrocarbons may also be used such as paraffin fractions containing a range of alkanes possibly with minor amounts of other hydrocarbons. Cycloaliphatic hydrocarbon such as methylcyclopentane may also be used. In a preferred aspect the feed to a process for preparing aromatic hydrocarbons and particularly benzene comprises hexanes. The temperature of the catalytic reaction may be from 370° C. to 600° C., preferably 430° C. to 550° C. and preferably pressures in excess of atmospheric are used, for example up to 2000 KPa, more preferably 500 to 1000 KPa. Hydrogen is employed in the formation of aromatic hydrocarbons preferably with a hydrogen to feed ratio of less than 10.

The process is preferably otherwise carried out in the manner described in U.S. Pat. No. 4,104,320 BE-A-888365, EP-A-40119, EP-A-142351, EP-A-145289 or EP-A-142352.

As shown in EP 96479, the use of zeolite L with cylindrical morphology enables greatly improved catalyst lifetimes to be achieved as compared to the lifetime obtained with a zeolite L, prepared according to the procedures described in the art prior to EP 96479. The invention enables macroscopic particles to be prepared from such cylindrical zeolite L, without the use of binder to dilute the performance of the cylindrical crystallites. The invention will now be described in more detail, though only by way of illustration, in the following Examples.

EXAMPLE 1

A) Preparation of Zeolite L According to EP 96479

A synthesis gel was prepared following the procedure of EP 96479 (but scaled up to synthesis in a 200 litre autoclave) having the following composition expressed in moles of pure oxide:

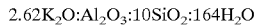

2.62$K_2O$:$Al_2O_3$:10$SiO_2$:164$H_2O$

This gel was crystallized at a temperature of 175° C. for 24 hours to bring about crystallization.

Figure 1B:
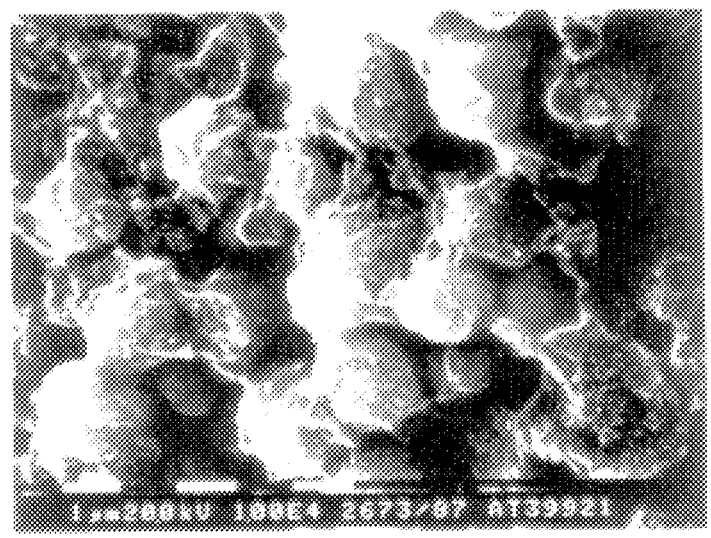
FIG. 1b shows the crystallites of FIG. 1a bound with silica.
Figure 1A:
FIG. 1a shows individual zeolite L crystallites as prepared in accordance with Ex. 1A.

The formed zeolite L was highly crystalline with a typical zeolite L X-ray diffraction (XRD) pattern. Scanning electron micrographs (SEM) show the product to be formed solely of well-defined cylindrical crystals having a particle size of from 1 to 2 microns as shown in FIG. 1a which is a scanning electron micrograph (SEM) with a magnification of 10000×.

B) Preparation of Particles

The product of A) above was formed into extrudates with silica as follows:

| Components used for preparation | Quantity (grams) |
|---|---|
| Zeolite L-crystals (dried after synthesis as in A) | 539.8 |
| $H_2O$ | 100.0 |
| Silica gel (PQCS -2040A) | 50.5 |
| Silica sol (Nalcoag -1037A) | 533.6 |
| Methocel (hydroxypropyl methyl cellulose extrusion aid) | 2.7 |

Wt % Solids

| | | |
|---|---|---|
| | Zeolite L | 69.7 |
| | $SiO_2$ | 30.0 |
| | Methocel | 0.35 |

(Total water content: 36%)

Preparation

The above components were mixed in a blender in the order shown

After about 5 minutes after adding the methocel a very thick and smooth paste was obtained, the total mixing time was 17 minutes. The resulting paste was packed in a polypropylene bag and extruded 2 days after preparation. After extrusion into 2mm extrudates, these extrudates were dried to remove residual water and then calcined in air at 500° C. for 3 hours. FIG. 1b is a 10000× SEM picture of the product.

C) Conversion to Binderless Zeolite L Particles of the Invention

A potassium aluminate solution was prepared from the following (weight chemicals in grams):

KOH pellets, purity 87.3%: 13.464
Al(OH)$_3$ pwdr, purity 98.5%: 9.339
$H_2O$: 84.25

The alumina was dissolved by boiling until a clear solution was obtained. The solution was cooled to room temperature and corrected for water loss due to boiling. The aluminate solution was quantitatively transferred into a 300 ml stainless steel autoclave. Next 75.17 gr silica-bound extrudates prepared in B) above, containing 30 wt % of silica binder and 3.4 wt % of adsorbed water, were added to the contents of the autoclave. The extrudates were used as is, and were not previously dried to remove adsorbed water. Some heat release was observed upon wetting the extrudates, however, the extrudates kept completely intact; there was no formation of fines in the supernatant liquid. The composition of the mixture in the autoclave, corrected for the water content of the extrudates, was:

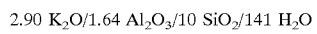

2.90 $K_2O$/1.64 $Al_2O_3$/10 $SiO_2$/141 $H_2O$

In this mixture the silica is present as the binder in the extrudate. The amount of KL-crystals in this mixture was 27.9 wt %, based on the total weight of the mixture.

The autoclave was heated up to 175° C. within 6 hrs and kept at this temperature for 63 hrs. After this ageing period the autoclave was opened and the product extrudates were collected.

It surprisingly appeared that the extrudates were intact; no formation of fines was observed. The extrudates were washed with 4 portions of 200 ml of water to remove residual mother liquor adhering to the surface of the extrudates. The thus prewashed extrudates were spread out in a Buechner funnel and the bed of extrudates was washed with two 300 ml portions of water, the flow of the water through the bed was about 80 mls/hr. The total washing time was about 7.5 hrs, the pH of the collected washwater was 8.5. The extrudates were dried for 4 hrs at 125° C. and for an additional 2 hrs at 200° C.

The weight increase of the recovered product-extrudates was 8.8 grams (corrected for the water content of the starting extrudates). According to the stoichiometry of the formation of zeolite L from the given composition of the synthesis mixture, the theoretical weight increase was calculated to be around 9.4 grams, hence the conversion of the silica into KL may be considered as virtually complete. The product extrudates were significantly harder than the starting extrudates.

The product-extrudates were characterized by XRD, SEM and toluene adsorption, with the following results:

XRD: % crystallinity increase vs starting extrudate: 40%, zeolite W-content (W/L ratio): Nil
SEM: (FIG. 1c, a 10000× SEM)

Surface of product extrudates consists of intergrown cylindrical crystallites with a diameter of about 1–2 microns, and some smaller new crystallites. There is no visible amorphous silica which is plainly visible in SEM of the starting extrudates. (FIG. 1b)

Toluene adsorption:
Starting extrudate: 6.5 wt % (at $p/p_o$—0.5) and 5.4 wt % (at $p/p_o$=0.25)
Product extrudate: 10.0 wt % (at $p/p_o$0.5 and $p/p_o$=0.25)
The toluene adsorption of the product equals that of pure zeolite L.

EXAMPLE 2

The above Example was repeated, but to the synthesis mixture was added 25 ppm of $Mg^{2+}$. The composition of this synthesis mixture was:

2.90 $K_2O$/1.63 $Al_2O_3$/10 $SiO_2$/141 $H_2O$+25 ppm $Mg^{2+}$

The synthesis condition (ageing, washing/recovery of product-extrudates) were as described above. The weight increase of the product extrudate was 80% of the calculated maximum increase.

XRD showed that the crystallinity was increased by 27% vs the starting extrudate and that no zeolite-W was present. SEM showed that the surface of the product extrudates consisted of about 1.5 micron crystallites together with very small crystallites with a diameter of about 0.2 microns. The toluene adsorption was 9.8% at $p/p_o$=0.5 and 8.8% at $p/p_o$=0.25.

EXAMPLE 3

Extrudates were prepared from cylindrical zeolite L crystallites, bound with 30 wt % (based on the weight of the extrudates) silica binder. 10.01 g of these extrudates were placed in an autoclave and a solution prepared from:

0.83 g aluminium hydroxide
1.77 g potassium hydroxide (87 wt %)
14.69 g deionized water added. After stirring the autoclave was closed and heated to 150° C. for 20 hours. The composition of the combined silica binder and aluminium hydroxide solution was:

2.75$K_2O$/1.06$Al_2O_3$/10$SiO_2$/172$H_2O$

SEM examination showed that the above treatment resulted in a change in appearance such as depicted in FIGS. 1b and 1c. The cyclohexane adsorption capacity was determined at 30° C. ($p/p_o$ cyclohexane=0.5) for the initial extrudates and the final product, and the results are as follows:

|  | Cyclohexane adsorption (wt %) |
| --- | --- |
| Original extrudates | 6.2 |
| Final product | 6.8 |

EXAMPLE 4: SYNTHESIS USING BARIUM

Using a similar procedure to Example 1, binderless zeolite L particles were prepared by mixing (in order)

| | |
| --- | --- |
| 3.38 g | KOH(87%) |
| 2.55 g | Al(OH)$_3$ |
| 0.033 g | Ba(OH)$_2$ 8H$_2$O |
| 20.11 g | water |
| 19.05 | silica bound extrudates of cylindrical zeolite L crystallites | as to give a gel composition (excluding preformed zeolite L but including binder) of 2.78$K_2O$/1.73$Al_2O_3$/0.01BaO/10$SiO_2$/126$H_2O$ This was crystallized at 175° C. for 24.5 hours, and the product washed to a pH of 9.2, then dried. 23.25 g of binderless zeolite L particles with excellent crushing strength were recovered. These particles showed 17% greater crystallinity than the initial extrudate, greater strength and a cyclohexane adsorption of 4.9 wt % ($p/p_o$=0.5, T=30° C.)

EXAMPLE 5

A 2 litre synthesis scaled up from Example 1 was carried out. The extrudates from Example 1B were treated as follows:

| | |
| --- | --- |
| 62.69 g | KOH(87%) |
| 43.47 g | Al(OH)$_3$(98.6%) |
| 391.14 g | water | were introduced into a 2 litre stainless steel autoclave and stirred to form a homogeneous solution. 350 g of the extrudate were added, and the autoclave was heated up to 175° C. over 6 hours and held at 175° C. for 63 hours. After cooling, the product was washed thoroughly, over 16 hours to pH 9.9, and then dried. 379 g of binderless zeolite L particles were recovered. SEM examination of the product showed similar results to FIG. 1c, except that the intergrown crystallites embedded in the binderless particle were somewhat larger at approximately 2 micron diameter. The toluene adsorption of this product was:

9.5 wt % (p/Po=0.25, T=3020 C.)

What is claimed is:

1. A process for the conversion of a hydrocarbon feed comprising contacting said feed with a catalyst comprising binderless zeolite L particles comprising cylindrical zeolite L crystallites with a mean diameter of at least 0.05 micron in a zeolite L matrix and a catalytically-active metal, said zeolite L particles prepared by first forming particles of a mixture of silica and from 10 to 95 wt % of performed zeolite L crystallites and thereafter reacting said mixture particles with an aqueous alkaline solution containing a source of alumina sufficient to convert the silica to zeolite L, in which the combined composition of the alkaline solution and the silica in the mixture particles is such that the molar ratio of $SiO_2$ to $Al_2O_3$ is in the range of 4–15.

2. The process of claim 1 wherein said conversion comprises a dehydrocyclization and/or isomerization process and wherein said feed comprises an acyclic hydrocarbon.

3. The process of claim 2 wherein said feed is contacted at a temperature of from 370° C. to 600° C.

4. The process of claim 3 wherein said catalytically active metal is at least one Group VIII metal having dehydrogenating activity to convert at least part of the acyclic hydrocarbons into aromatic hydrocarbons.

5. The process of claim 1 wherein said mixture particles contain from 10 to 50 wt % of said preformed zeolite L crystallites.

6. The process of claim 1 wherein the combined composition of the alkaline solution and the silica in the mixture particles is within the following molar ratios, expressed as oxides:

| | |
|---|---|
| $(M_2O + M^1_{2/n}O)/SiO_2$ | 0.18–0.36 |
| $H_2O/(M_2O + M^1_{2/n}O)$ | 25–90 |
| $SiO_2/Al_2O_3$ | 4–15 |
| $M_2O/(M_2O + M^1_{2/n}O)$ | 0.9–1 | wherein M is potassium, $M^1$ is copper, magnesium, calcium, barium, lead, manganese, chromium, cobalt, nickel or zinc cation and n is the valence of $M^1$.

7. The process of claim 6 in which the combined composition is:

$$2.5-3.2K_2O/1.5-2.5Al_2O_3/10SiO_2/120-180H_2O.$$

8. The process of claim 6 wherein the molar ratio $(M_2 + M^1_{2/n}O)/SiO_2$ is 0.25 to 0.35 and the molar ratio $SiO_2/Al_2O_3$ is 5–8.

9. The process of claim 6 wherein potassium is replaced by up to 30 mol % of another alkali metal.

10. The process of claim 1 wherein said aqueous alkaline solution is free of an additional source of silica.

* * * * *